(12) United States Patent
Bittman et al.

(10) Patent No.: US 9,359,389 B2
(45) Date of Patent: Jun. 7, 2016

(54) CAGED CERAMIDE-1-PHOSPHATE DERIVATIVES

(75) Inventors: Robert Bittman, Roslyn Heights, NY (US); Antonio Gomez Munoz, Leioa (ES)

(73) Assignee: RESEARCH FOUNDATION OF THE CITY UNIVERSITY OF NEW YORK, New York, NY (US)

( * ) Notice: Subject to any disclaimer, the term of this patent is extended or adjusted under 35 U.S.C. 154(b) by 441 days.

(21) Appl. No.: 13/504,206

(22) PCT Filed: Oct. 26, 2010

(86) PCT No.: PCT/US2010/054145
§ 371 (c)(1),
(2), (4) Date: Jun. 6, 2012

(87) PCT Pub. No.: WO2011/056599
PCT Pub. Date: May 12, 2011

(65) Prior Publication Data
US 2012/0238018 A1    Sep. 20, 2012

Related U.S. Application Data

(60) Provisional application No. 61/254,993, filed on Oct. 26, 2009.

(51) Int. Cl.
| | | |
|---|---|---|
| *C12N 5/02* | (2006.01) |
| *C07F 9/09* | (2006.01) |
| *A61K 31/661* | (2006.01) |
| *C07F 9/24* | (2006.01) |
| *C07F 9/653* | (2006.01) |
| *C07F 9/655* | (2006.01) |

(52) U.S. Cl.
CPC .............. *C07F 9/094* (2013.01); *A61K 31/661* (2013.01); *C07F 9/091* (2013.01); *C07F 9/2408* (2013.01); *C07F 9/2429* (2013.01); *C07F 9/653* (2013.01); *C07F 9/65522* (2013.01)

(58) Field of Classification Search
CPC ..... A61K 31/661; C07F 9/094; C07F 9/2408; C07F 9/2429; C07F 9/652; C07F 9/65522
See application file for complete search history.

(56) References Cited

U.S. PATENT DOCUMENTS

| 6,472,541 B2 | 10/2002 | Tsien et al. |
| 7,304,168 B2 | 12/2007 | Li et al. |
| 7,432,368 B2 | 10/2008 | Stengele |

OTHER PUBLICATIONS

Lankalapalli et al. (Coumarin-4-yl)methyl esters as cages of phospholipid second messengers Abstracts of Papers, presented at the 236th ACS national Meeting Philadelphis PA, Aug. 17-21, 2008.*
Lankalapalli et al., "Caged Ceramide 1-Phosphate Analogues: Synthesis and Properties", J. Org. Chem., 74(22) pp. 8844-8847 (2009).
Qiao et al., "Synthesis and Evaluation of a Photolyzable Derivative of Sphingosine 1-Phosphate-Caged SPP", Bioorganic & Medicinal Chemistry Letters 8, pp. 711-714 (1998), published on-line Oct. 26, 2009.
Gutknecht et al., "Ionic Permeability of Thin Lipid Membranes", The Journal of General Physiology, vol. 55, pp. 359-374 (1970).
Melan et al., "Redistribution and Differential Extraction of Soluble Proteins in Permeabilized Cultured Cells—Implications for Immunofluorescence Microscopy", Journal of Cell Science 101, pp. 731-743 (1992).
Fyrst et al., "An Update on Sphingosine-1-Phosphate and Other Sphingolipid Mediators", Nature Chemical Biology, vol. 6, pp. 489-497 (2010).
Tauzin et al., "Effects of Ceramide-1-Phosphate on Cultured Cells: Dependence on Dodecane in the Vehicle", Journal of Lipid Research, vol. 48, pp. 66-76 (2007).
Gomez-Munoz et al., Stimulation of DNA Synthesis of Natural Ceramide 1-Phosphate, Biochem J., 325, pp. 435-440 (1997).
Gomez-Munoz et al., "Ceramide-1-Phosphate Promotes Cell Survival Through Activation of the Phosphatidylinositol 3-Kinase/Protein Kinase B Pathway", FEBS Letters 579, pp. 3744-3750 (2005).
Gomez-Munoz et al., Short-Chain Ceramide-1-Phosphates are Novel Stimulators of DNA Synthesis and Cell Division: Antagonism by Cell-Permeable Ceramides, Molecular Pharmacology, 47:883-889 (1995).

* cited by examiner

*Primary Examiner* — Susan Hanley
(74) *Attorney, Agent, or Firm* — Hoffmann & Baron, LLP (57) ABSTRACT

The invention relates to novel caged ceramide 1-phosphate (C1P), caged ceramide 1-phosphate derivatives(C1P), and the method of using them for delivering C1P intracellularly in vitro and in vivo, for research and therapeutic purposes. Therapeutic purposes include treatment of diseases associated with cell death, such as neurodegerative diseases, including Alzheimer's disease. The disclosed compositions may also be used for wound healing.

16 Claims, 4 Drawing Sheets

N-palmitoyl-C1P $R_1 = H, R_2 = COC_{15}H_{31}$
1 $R_1 = DECM, R_2 = H$
1a $R_1 = DECM, R_2 = COC_{15}H_{31}$
2 $R_1 = BHNB, R_2 = H$
2a $R_1 = BHNB, R_2 = COC_{15}H_{31}$

DECM          BHNB

CAGED CERAMIDE-1-PHOSPHATE DERIVATIVES

CROSS-REFERENCE TO RELATED APPLICATION

The present application claims priority from U.S. Provisional Application Ser. No. 61/254,993, filed on Oct. 26, 2009.

GOVERNMENT RIGHTS

The invention was funded by NIH grant # HL083187. The United States government has certain rights in this invention.

FIELD OF THE INVENTION

This invention relates to novel caged ceramide 1-phosphate (C1P) and the method of using them for delivering C1P intracellularly in vitro and in vivo, for research and therapeutic purposes.

BACKGROUND OF THE INVENTION

Ceramide-1-phosphate (C1P), the product of ceramide kinase, is a sphingophospholipid with recently recognized important signaling properties. In particular, it was reported to have mitogenic activity, and to be capable of direct stimulation of cytosolic phospholipase A (2α). C1P has been observed to be able to stimulate cell division, induce DNA synthesis, block apoptosis and promote cell survival. It has been recognized as one of the most important mediators that affect the physiology of cells, and has caused much interest in using it as a potential therapeutic agent.

Accordingly, there is currently much research into the properties and use of C1P. However, delivering C1P intracellularly, the actual loci of its action, is not trivial. Previous research into C1P has relied on the use of C1P of various acyl chain lengths and diverse protocols to deliver it to cultured cells. Typically, intracellular delivery of C1P was achieved by adding the lipid in a mixture of alcohol/dodecane. Most commonly, a mixture of ethanol or methanol with dodecane is used as the vehicle.

However, it has been reported that the inclusion of dodecane in this method induces artifacts in the cells, thereby rendering many observed effects of C1P unreliable. See, for example, Gómez-Muñoz et al., FEBS Letters 579, 3744-3750 (2005).

Another method that has been employed to introduce C1P into the cytosol is to produce C1P in situ by transfecting cells with ceramide kinase, the enzyme that catalyzes the phosphorylation of ceramide. However, many cells cannot be transfected (such as primary bone marrow-derived macrophages).

The difficulty in delivering C1P to intracellular compartments has contributed to the lack of progress with this important molecule both as a research target and as a therapeutic agent. As a result, much of C1P signaling is still poorly understood.

Although these problems were acknowledged at least as early as 2005, see above, a solution has heretofore not been found.

SUMMARY OF THE INVENTION

In a first embodiment, the invention relates to a D-erythro ceramide-1-phosphate derivative having formula 1, wherein:
$R^1$ represents a benzhydryl derivative having formula 2 or a coumarinyl-4-methyl derivative having formula 3;
$R^3$ represents H or a benzhydryl derivative having formula 2 or a coumarinyl-4-methyl derivative having formula 3;

n is 12 or 14
$R^2$ represents a fatty acyl group having formula 4

$R^4$ represents H or OH;
$R^5$ represents a saturated or unsaturated aliphatic group having 12-22 carbon atoms;
Y and Z independently represent H, Cl, Br, OH, $OCH_3$, or triazolyl, in which case at least one of Y or Z represents OH; or Y and Z join together to form a 5 or 6 member carbocyclic or heterocyclic ring that is optionally fused to a second 5 or 6 member carbocyclic or heterocyclic ring, wherein the second 5 or 6 member carbocyclic or heterocyclic ring is optionally fused to a third 5 or 6 member carbocyclic or heterocyclic ring, and wherein any of the carbocyclic or heterocyclic rings are optionally substituted with one or more functional groups selected from the group consisting of methyl, OH, $OCH_3$, Cl, Br, $NO_2$, $NMe_2$, and $NEt_2$;
$Ar^1$ represents phenyl, or phenyl substituted with one or more functional groups selected from the group consisting of $NMe_2$, $NEt_2$, OH, and $OCH_3$;
V, W, and X independently represent H, Cl, Br, OH, $OCH_3$, $NMe_2$, $NEt_2$ or $Ar^2$; and
$Ar^2$ represents phenyl, or phenyl substituted with one or more functional groups selected from the group consisting of OH, $OCH_3$, $NMe_2$, $NEt_2$, triazolyl, and phenyltriazolyl.

Some additional embodiments include the following:

2. embodiment 1, wherein $R^3$ and $R^4$ represent H.
3. embodiment 1, wherein $R^1$ represents a benzhydryl derivative having formula 2 and $R^3$ represents H or a benzhydryl derivative having formula 2.
4. embodiment 3, wherein Y and Z independently represent H, Cl, Br, OH, $OCH_3$, or triazolyl.
5. embodiment 3, wherein Y and Z independently represent Cl, Br, OH, or $OCH_3$.
6. embodiment 3, wherein Y and Z independently represent Br or OH.
7. embodiment 2, wherein $R^1$ represents a benzhydryl derivative having formula 2, Y represents OH and Z represents Br.
8. embodiment 7, wherein $Ar^1$ represents phenyl.
9. embodiment 8, wherein $R^5$ represents —$(CH_2)_{13}$—$CH_3$.
10. embodiment 1, wherein $R^1$ represents a coumarinyl-4-methyl derivative having formula 3 and $R^3$ represents H or a coumarinyl-4-methyl derivative having formula 3.
11. embodiment 10, wherein V, W, or X represents $NMe_2$ or $NEt_2$.
12. embodiment 10, wherein V and X represent H, and W represents $NMe_2$ or $NEt_2$.
13. embodiment 2, wherein $R^1$ represents a coumarinyl-4-methyl derivative having formula 3, V and X represent H, and W represents $NMe_2$ or $NEt_2$.
14. embodiment 13, wherein $R^5$ represents —$(CH_2)_{13}$—$CH_3$.
15. embodiment 1 used in a method for introducing a ceramide-1-phosphate molecule into a biological cell, the method comprising exposing the cell to a D-erythro ceramide-1-phosphate derivative having formula 1, wherein:
$R^1$ represents a benzhydryl derivative having formula 2 or a coumarinyl-4-methyl derivative having formula 3;
$R^3$ represents H or a benzhydryl derivative having formula 2 or a coumarinyl-4-methyl derivative having formula 3;

n is 12 or 14
$R^2$ represents a fatty acyl group having formula 4

$R^4$ represents H or OH;
$R^5$ represents a saturated or unsaturated aliphatic group having 12-22 carbon atoms;
Y and Z independently represent H, Cl, Br, OH, $OCH_3$, or triazolyl, in which case at least one of Y or Z represents OH; or Y and Z join together to form a 5 or 6 member carbocyclic or heterocyclic ring that is optionally fused to a second 5 or 6 member carbocyclic or heterocyclic ring, wherein the second 5 or 6 member carbocyclic or heterocyclic ring is optionally fused to a third 5 or 6 member carbocyclic or heterocyclic ring, and wherein any of the carbocyclic or heterocyclic rings are optionally substituted with one or more functional groups selected from the group consisting of methyl, OH, $OCH_3$, Cl, Br, $NO_2$, $NMe_2$, and $NEt_2$;
$Ar^1$ represents phenyl, or phenyl substituted with one or more functional groups selected from the group consisting of $NMe_2$, $NEt_2$, OH, and $OCH_3$;
V, W, and X independently represent H, Cl, Br, OH, $OCH_3$, $NMe_2$, $NEt_2$ or $Ar^2$; and
$Ar^2$ represents phenyl, or phenyl substituted with one or more functional groups selected from the group consisting of OH, $OCH_3$, $NMe_2$, $NEt_2$, triazolyl, and phenyl-triazolyl.
16. embodiment 15, wherein $R^3$ and $R^4$ represent H.
17. embodiment 16, wherein $R^1$ represents a benzhydryl derivative having formula 2 and $R^3$ represents H or a benzhydryl derivative having formula 2.
18. embodiment 17, wherein Y and Z independently represent H, Cl, Br, OH, $OCH_3$, or triazolyl.
19. embodiment 17, wherein Y and Z independently represent Cl, Br, OH, or $OCH_3$.
20. embodiment 17, wherein Y and Z independently represent Br or OH.
21. embodiment 16, wherein $R^1$ represents a benzhydryl derivative having formula 2, Y represents OH and Z represents Br.
22. embodiment 21, wherein $Ar^1$ represents phenyl.
23. embodiment 22, wherein $R^5$ represents —$(CH_2)_{13}$—$CH_3$.
24. embodiment 15, wherein $R^1$ represents a coumarinyl-4-methyl derivative having formula 3 and $R^3$ represents H or a coumarinyl-4-methyl derivative having formula 3.

25. embodiment 24, wherein V, W, or X represents NMe$_2$ or NEt$_2$.
26. embodiment 24, wherein V and X represent H, and W represents NMe$_2$ or NEt$_2$.
27. embodiment 16, wherein R$^1$ represents a coumarinyl-4-methyl derivative having formula 3, V and X represent H, and W represents NMe$_2$ or NEt$_2$.
28. embodiment 27, wherein R$^5$ represents —(CH$_2$)$_{13}$—CH$_3$.

BRIEF DESCRIPTION OF THE DRAWINGS

FIG. 2 shows structures of C1P, DECM- and BHNB-Caged S1P Analogues 1 and 2, and C1P Analogues 1a and 2a.

DETAILED DESCRIPTION

The invention relates to caged ceramide-1-phosphate (C1P) compounds. A D-erythro ceraminde-1-phosphate derivative having formula 1 below is claimed.

R$^1$ represents a benzhydryl derivative having formula 2 or a coumarinyl-4-methyl derivative having formula 3 below.

R$^3$ represents H or a benzhydryl derivative having formula 2 or a coumarinyl-4-methyl derivative having formula 3.

The letter n is 12 or 14

R$^2$ represents a fatty acyl group having formula 4.

R$^4$ represents H or OH. In a preferred embodiment, R$^3$ and R$^4$ represent H.

R$^5$ represents a saturated or unsaturated aliphatic group that has 12-22 carbon atoms, and that is part of fatty acyl group R$^2$. Some examples of saturated aliphatic groups include n-dodecanyl, n-tridecanyl, n-tetradecanyl, n-pentadecanyl, n-hexadecanyl, n-heptadecanyl, n-octadecanyl, n-nonadecanyl, n-icosanyl, 4-methyldodecanyl, and 3-ethyl-5-methylpentadecanyl.

The unsaturated alkyl groups of R$^5$ are such that the fatty acyl groups R$^2$ are those commonly found in fatty acids, e.g., oleic acid, linoleic acid, linolenic acid.

In a preferred embodiment, R$^5$ represents —(CH$_2$)$_{13}$—CH$_3$.

In another embodiment, R$^1$ represents a benzhydryl derivative having formula 2 and R$^3$ represents H or a benzhydryl derivative having formula 2. In this embodiment, Y and Z independently represent H, Cl, Br, OH, OCH$_3$, or triazolyl, in which case at least one of Y or Z represents OH. For example, if Y is Cl, then Z must be OH. Likewise, if Z is Br, then Y is OH. Preferably, Y and Z independently represent Br or OH.

Alternatively, Y and Z join together to form a fused 5 or 6 member carbocyclic or heterocyclic ring that is optionally fused to a second 5 or 6 member carbocyclic or heterocyclic ring, wherein the second 5 or 6 member carbocyclic or heterocyclic ring is optionally fused to a third 5 or 6 member carbocyclic or heterocyclic ring, and wherein any of the carbocyclic or heterocyclic rings are optionally substituted with one or more functional groups selected from the group consisting of methyl, OH, OCH$_3$, Cl, Br, NO$_2$, NMe$_2$, and NEt$_2$. Therefore, the ring systems are monocyclic, bicyclic, or tricyclic. The 5 or 6 member carbocyclic or heterocyclic rings may or may not be aromatic.

Carbocyclic rings, for example, may be cyclopentano, cyclohexano, and benzo. Examples of fused carbocyclic rings include indeno, isoindeno, and naphtheno.

Heterocyclic rings include one or more N, O, or S ring atom, and include pyrrolidino, piperidino, piperazino, tetrahydrofurano, morpholino, oxazolidino, furano, pyrrole, pyrazole, imidazole, oxazole, thiazole, triazole, pyridino, pyridazino, pyrimidino, and pyrazino. Examples of fused heterocyclic rings include benzomorpholino, benzopyrrolidino, indolino, benzopiperidino, purino, 1,4-diazanaphthaleno, indolo, benzimidazole, 4,5-diazaphenbenzo, isoindolo, quinolino, isoquinolino, and benzofurano.

Further examples of fused heterocyclic ring systems having at least one carbocyclic ring and at least one heterocyclic ring include benzofurano, benzoxazolo, and pyrrolobenzo.

$Ar^1$ represents phenyl, or phenyl substituted with one or more functional groups selected from the group consisting of $NMe_2$, $NEt_2$, OH, and $OCH_3$. In a preferred embodiment, $Ar^1$ represents phenyl.

In another embodiment, $R^1$ represents a derivative having formula 3 and $R^3$ represents H or a derivative having formula 3.

In this embodiment, V, W, and X independently represent H, Cl, Br, OH, $OCH_3$, $NMe_2$, $NEt_2$ or $Ar^2$. In one preferred embodiment, V, W, and X represent $NMe_2$ or $NEt_2$. In another preferred embodiment, V and X represent H and W represents $NMe_2$ or $NEt_2$.

$Ar^2$ represents phenyl, or phenyl substituted with one or more functional groups selected from the group consisting of OH, $OCH_3$, $NMe_2$, $NEt_2$, triazolyl, and phenyltriazolyl.

In one preferred embodiment, $R^1$ represents a derivative having formula 2, Y represents OH, and Z represents Br. In another preferred embodiment, $R^1$ represents a derivative having formula 3, V and X represent H, and W represents $NMe_2$ or $NEt_2$.

The invention also relates to a method for introducing a ceramide-1-phosphate molecule into a biological cell by exposing the cell to any of the D-erythro ceramide-1-phosphate derivatives described above. The D-erythro ceramide-1-phosphate derivative is described above. The method involves use of the caged compounds in aqueous buffer under physiological conditions.

In this specification, groups of various parameters containing multiple members are described. Within a group of parameters, each member may be combined with any one or more of the other members to make additional sub-groups. For example, if the members of a group are a, b, c, d, and e, additional sub-groups specifically contemplated include any two, three, or four of the members, e.g., a and c; a, d, and e; b, c, d, and e; etc.

In some cases, the members of a first group of parameters, e.g., a, b, c, d, and e, may be combined with the members of a second group of parameters, e.g., A, B, C, D, and E. Any member of the first group or of a sub-group thereof may be combined with any member of the second group or of a sub-group thereof to form additional groups, i.e., b with C; a and c with B, D, and E, etc.

For example, in the present invention, groups of various parameters are defined (e.g. $R^1$, $R^2$, $R^3$, $R^4$, $R^5$, $Ar^1$, $Ar^2$, V, W, and X). Each group contains multiple members. For example, V, W, and X independently represent H, Cl, Br, OH, $OCH_3$, $NMe_2$, $Net_2$, or $Ar^2$. Each member may be combined with each other member to form additional sub-groups, e.g., H and Cl, OH and $NMe_2$, or $OCH_3$ and $Ar^2$.

The instant invention further contemplates embodiments in which each element listed under one group may be combined with each and every element listed under any other group. For example, $R^1$ is identified above as representing a benzhydryl derivative having formula 2 or a coumarinyl-4-methyl derivative having formula 3. $R^3$ is identified above as representing H or a benzhydryl derivative having formula 2 or a coumarinyl-4-methyl derivative having formula 3. Each element of $R^1$ (a benzhydryl derivative having formula 2 or a coumarinyl-4-methyl derivative having formula 3) can be combined with each and every element of $R^3$ (H or a benzhydryl derivative having formula 2 or a coumarinyl-4-methyl derivative having formula 3). For example, in one embodiment, $R^1$ and $R^2$ may represent a coumarinyl-4-methyl derivative having formula 3. Alternatively, $R^1$ may represent a benzhydryl derivative having formula 2 and $R^2$ may represent H, etc. Similarly, a third group is n, in which the elements are defined as 12 or 14. Each of the above embodiments may be combined with each and every element of n. For example, in the embodiment wherein $R^1$ and $R^2$ represent a coumarinyl-4-methyl derivative having formula 3, n may be 12 (or any other number within the element of n).

With each group, it is specifically contemplated that any one of more members can be excluded. For example, if V, W, and X are defined as H, Cl, Br, OH, $OCH_3$, $NMe_2$, $NEt_2$, or $Ar^2$, it is also contemplated that V, W, and X are defined as H, OH, $OCH_3$, or $NEt_2$.

The compounds of this invention are limited to those that are chemically feasible and stable. Therefore, a combination of substituents or variables in the compounds described above is permissible only if such a combination results in a stable or chemically feasible compound. A stable compound or chemically feasible compound is one in which the chemical structure is not substantially altered when kept at a temperature of 40° C. or less, in the absence of moisture or other chemically reactive conditions, for at least a week.

A list following the word "comprising" is inclusive or open-ended, i.e., the list may or may not include additional unrecited elements. A list following the words "consisting of" is exclusive or closed ended, i.e., the list excludes any element not specified in the list.

The DECM- or BHNB-caged analogs of the invention permit intracellular delivery of ceramide 1-phosphate into different cell types, including primary bone marrow-derived macrophages. The synthesis of the caged C1P compounds as well as their testing for intracellular delivery through photochemical uncaging are disclosed in detail below.

Figure 1A:
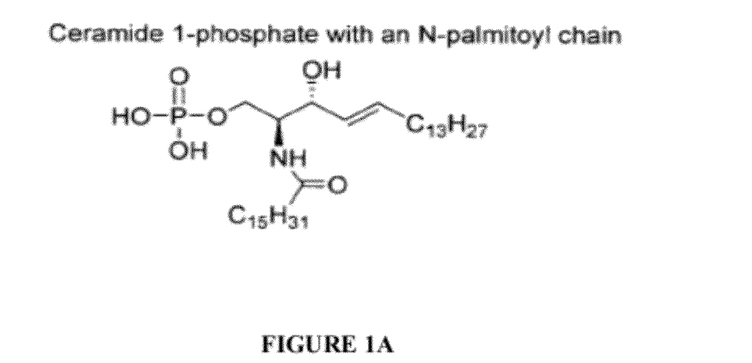
FIG. 1A shows a structure of ceramide l-phosphate.

Natural C1P has a mixture of fatty amide chains. FIG. 1A, shows an example in which the amide chain is palmitoyl. Also, the structure and process of making the caged C1P with 4-bromo-5-hydroxy-2-nitrobenzhydryl (BHNB) group is shown, but a similar process to make other analogs in which the Ph ring is replaced with other aryl groups can also be used.

Since C1P is a lipid mediator that promotes cell survival under stress conditions, the caged C1P analogs can be used to deliver C1P for therapeutic purposes. Such purposes include treating diseases that are associated with cell death, such as neurodegenerative diseases (caused by neuronal death) including Alzheimer's disease.

Since ceramide 1-phosphate stimulates proliferation of skin fibroblasts and myoblasts, the caged C1P analogs can be used for delivering C1P as a therapeutic agent for wound healing.

C1P is a selective inhibitor of ceramide accumulation in cells, as it blocks the activities of acid and neutral sphingomyelinases and serine-palmitoyl transferase. The caged C1P analogs can be used for opposing the pro-apoptotic actions of ceramide.

Activation of acid sphingomyelinase (ASMase), which produces ceramides from degradation of sphingomyelin, has been shown to play a role in sepsis, as it facilitates infection and spread of various bacterial and viral pathogens. For example, *Pseudomonas aeruginosa, Nisseria gonorrhoeae*, and rhinovirus all require a membrane composition change that includes increasing the number and size of ceramide-rich microdomains.

Since C1P blocks the activities of ASMase, the caged C1P analogs can be used to deliver C1P for treating the infectious actions of these microorganisms through inhibition of ASMase.

Emphysema is a chronic, obstructive pulmonary disease, and ceramides are crucial mediators of alveolar destruction in emphysema. Therefore, the caged ceramide 1-phosphate analogs can be used for delivering C1P for treating this disease through inhibition of ASMase and ceramide accumulation.

ASMase plays a critical role in cardiovascular disease and diabetes. Patients with type 2 diabetes have elevated levels of plasma ASMase, and this has been linked to increased risk of atherosclerosis. In addition, ceramides have been associated with increased insulin resistance. The caged ceramide 1-phosphate analogs can be used for delivering C1P for treating diabetes.

ASMase activity is higher than normal in patients with major depressive episodes. Inhibition of ASMase by the caged ceramide 1-phosphate analogs can be used for treatment of depression.

The caged C1P analogs can be used to offset C1P's activities to enhance cytosolic phospholipase A2 (cPLA2), increase intracellular calcium level, or to enhance COX activity and the production of proinflammatory eicosanoids.

The caged C1P compounds may also have utility as antidiabetes compounds. C1P stimulates incorporation of glucose into macrophages (and perhaps other cells) although this is a receptor-mediated event. This finding supports the idea that C1P may act as an anti-diabetes compound, although through a mechanism distinct to that of intracellular C1P.

Applicants have developed novel caged C1P compounds to easily and safely deliver C1P intracellularly, without any cytotoxic effects. The caged C1P molecules can pass through the intact plasma membrane of living cells spontaneously and accumulate in the cell interior without markedly reducing the cell viability. The caged molecules can be excited by methods known in the art, such as with one-photon absorption using wavelengths of approximately 360 nm to 520 nm, or with two-photon excitation using light with wavelengths between about 640 nm and 900 nm.

Applicants are able to efficiently deliver C1P intracellularly through photochemical uncaging process of these compounds in cells. These compounds would be greatly useful for research C1P in cells and tissues in vitro and in vivo, where other delivery methods are either not successful or not specifically localized. In addition, the caged C1P analogs can also be used to deliver C1P as a therapeutic agent intracellularly to stimulate cell growth, promote cell survival, inhibit apoptosis, and reduce inflammation in various disease settings.

General Synthetic Methods

Figure 2:
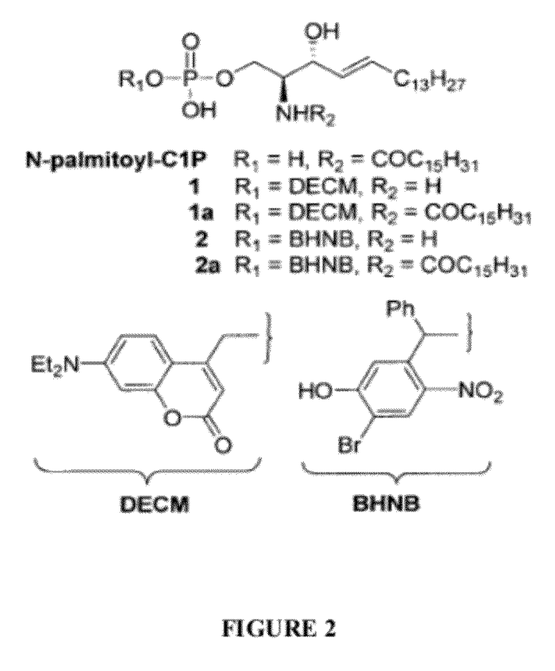

Suitable syntheses of structures 1, 1a, 2, and 2a shown in FIG. 2 are described below. Other compounds of the invention can be synthesized by adapting similar methods, some of which are described in more detail in the specific examples.

FIG. 2 represents the synthesis of caged S1P (1, 2) and C1P (1a, 2a) analogues in which the phosphate headgroup is esterified to a 7-(diethylamino)coumarin (DECM) or 4-bromo-5-hydroxy-2-nitrobenzhydryl (BHNB) group. The ability of caged C1P conjugates 1a and 2a to deliver C1P into mammalian cell cultures on exposure to visible light was assessed. Photochemical uncaging of C1P may be particularly useful in cells that cannot be transfected with specific enzymes as in primary bone marrow derived macrophage (BMDM) cell types, and to distinguish between intracellular and cell surface receptor-mediated activities.

Scheme 1. Synthesis of Phosphoramidite 8

For the synthesis of the DECM-caged S1P 1 and C1P 1a, (S)-Garner aldehyde 3 (Scheme 1) was treated with vinylmagnesium bromide at −78° C. to provide a 6:1 mixture of erythro alcohol 4 and its C3-epimer 4a. Alcohol 4 was purified by chromatography (hexane/EtOAc 5:1), and the hydroxy group was protected as its MOM ether 5. The oxazolidine group was selectively deprotected using 1 M HCl in THF at rt to give N-Boc-3-O-MOM-protected alcohol 6. An E-selective cross metathesis of olefin 6 with 1-pentadecene using Grubbs' second-generation catalyst afforded the 3-MOM ether of (2S,3R)-N-Boc-sphingosine 7. Sphingosine derivative 7 was treated with i-Pr$_2$NP(OMe)Cl in the presence of DIPEA to provide phosphoramidite intermediate 8.

Scheme 2. Synthesis of DECM-C1P Analogue 1a

7-(Diethylamino)-4-hydroxymethylcoumarin (9) was prepared by oxidation of 4-methyl-7-(diethylamino)coumarin with $SeO_2$, and subsequent reduction with $NaBH_4$. Reaction of alcohol 9 with phosphoramidite 8 in the presence of 1H-tetrazole provided a phosphite intermediate, which was oxidized in the same pot with anhydrous TBHP to afford phosphate 10 (Scheme 2). Removal of the protecting groups required some exploration. An initial attempt to deprotect both the Boc and MOM groups with TFA resulted in the loss of the Boc group in 1 h; however, only 50% of the MOM group was removed even after stirring for 3 days at rt. Reaction with $Me_3SiBr$ in $CH_2Cl_2$, rather than removing the methyl ester of the phosphate, resulted instead in the loss of the coumarin moiety from the lipid. When 10 was heated in 6 M HCl/THF (2:1) at 60° C. for 6 h, all three groups, Boc, MOM, and the phosphate methyl ester, were removed to provide DECM-S1P (1), which on neutralization and N-acylation using p-nitrophenyl palmitate in $DMF/CH_2Cl_2$ gave C1P analogue 1a in good yield.

To provide caged phospholipids with a high molar absorptivity at longer wavelengths than 1 and 1a, BHNB-caged compounds 2 and 2a were prepared. Bromo and nitro groups were selected as the electron-withdrawing groups, with the nitro group positioned ortho to the benzhydryl carbon to facilitate photorelease of the phosphorylated sphingolipid. The first step in the preparation of the BHNB cage was bromination of 4-methoxy-2-methyl-1-nitrobenzene (11, Scheme 3). When 11 was heated with NBS overnight at reflux in MeCN, a substantial amount of the starting material was observed along with the product. However, when a pressure tube was used for this reaction, heating at 140° C. overnight resulted in a mixture of the desired brominated product 12 together with unseparable by-products, and no starting material. A known method for the conversion of a methyl group in the ortho position to a nitro group to an aldehyde was used. Therefore, reaction of 12 with DMF dimethyl acetal (DMF-DMA), followed by oxidation of the intermediate enamine with $NaIO_4$, successfully converted 12 to aldehyde 13. After the by-products were removed by chromatography, addition of PhMgBr to 13 afforded the desired caged benzhydryl alcohol 14. A reaction time of 30 min at −78° C. is critical for this addition reaction, as decomposition of compound 14 was observed after 30 min.

After alcohol 14 was converted to phosphoramidite 15 with i-$Pr_2NP(OMe)Cl$ (Scheme 3), coupling with sphingosine derivative 16 (Scheme 4) in the presence of 1H-tetrazole afforded 17. Phosphite 17 was purified by flash chromatography prior to oxidation because the corresponding phosphate co-eluted with excess alcohol 16. Oxidation of 17 with TBHP afforded phosphate 18 in 70% yield over three steps. Several reagents ($BBr_3$ in $CH_2Cl_2$ at −78 °C., 33% HBr in AcOH at 0° C., 1 M HCl/THF (1:1) at rt, and TMSBr in $CH_2Cl_2$) to remove the protecting groups in 18 were screened unsuccessfully. Use of excess LiI in pyridine at reflux was successful, resulting in O-demethylation of both the anisole methyl group and phosphate methyl ester groups of 18, affording 19 in 90% yield. Reaction of 19 with 3 M HCl/MeOH/$CH_2Cl_2$ (1:2:1) at gentle reflux for 2.5 h provided BHNB-caged S1P 2. N-Acylation with p-nitrophenyl palmitate gave C1P analogue 2a in 77% yield.

Scheme 3. Synthesis of Benzhydryl Alcohol 14 and Phosphoramidite 15

Scheme 4. Synthesis of BHNB-caged C1P Analogue 2a

Figure 3A:
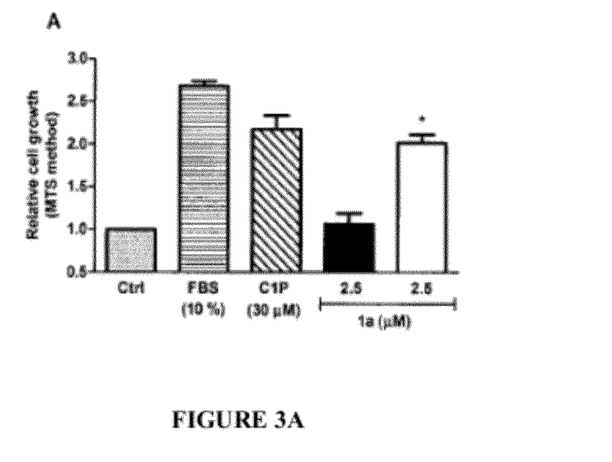
FIG. 3A shows delivery of 1a and 2a into RAW 264.7 macrophages stimulates cell growth. The open bars show the results for cells exposed to 400-500 nm light in a transilluminator. The filled bars show the results for cells incubated in the dark with the compounds.
Figure 3B:
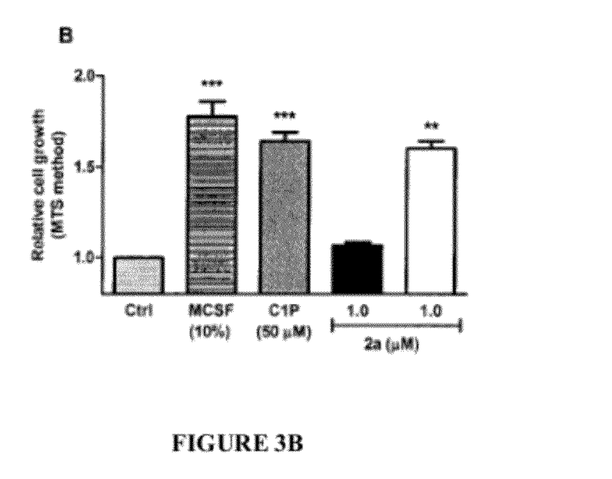
FIG. 3B shows the results for delivery of 1a and 2a into primary BMDM cells. The cells were incubated with 1.5% MCSF for 24 hr.

FIGS. 3A and 3B show a comparison of the effects of adding growth factors, N-palmitoyl-C1 P (30 or 50 μM, as an aqueous dispersion), 1a (2.5 μM in EtOH), and 2a (1.0 μM in EtOH) to RAW264.7 (panel A) or primary BMDM (panel B). Compounds 1a and 2a stimulated cell division, as determined by the MTS assay, at 2.5 and 1.0 μM, respectively, on exposure of the cells to light. To achieve the same relative level of RAW264.7 and BMDM cell growth with exogenous C1P, optimum concentrations of 30 and 50 μM were required, respectively. 1a, at 2.5 μM, was as potent as exogenous C1P at 30 μM. The putative photo by -product formed on photolysis of 1a (compound 9) did not stimulate cell proliferation, nor did an analogue of the photo by-product 20 formed on photolysis of 2a. No growth stimulation was observed in the dark.

In conclusion, 1a and 2a, the first caged analogues of C1P, were prepared and found to release C1P intracellularly, as demonstrated by stimulation of macrophage proliferation at significantly lower concentrations than exogenous C1P. These compounds, and their N-acyl variants, are likely to find utility as research tools for investigating the intracellular activities of this important lipid second messenger.

EXAMPLES (4S,5R,1"E)-tert-Butyl-4-(((((4'-bromo-5'-hydroxy-2'-nitrophenyl)(phenyl)methoxy) (hydroxy)phosphoryloxy)methyl)-2,2-dimethyl-5-(pentadec-1"-enyl)oxazolidine -3-carboxylate (19). A solution of 18 (48 mg, 0.056 mmol) and anhydrous LiI (150 mg, 1.12 mmol) in dry py (5 mL) was heated at reflux overnight. The reaction was quenched with saturated aq NH$_4$Cl solution (15 mL), and the product was extracted with CH$_2$Cl$_2$ (3 ×15 mL), dried (Na$_2$SO$_4$), concentrated, and purified by chromatography (CHCl$_3$/MeOH 3:1) to afford 19 (37 mg, 90%): R$_f$ 0.60 (CHCl$_3$/MeOH 3:1); $^1$H NMR (CD$_3$OD) δ 0.78 (t, 3H, J=6.6 Hz), 1.18 (m, 31H), 1.38 (m, 6H), 1.90 (m, 2H), 3.79 (m, 3H), 4.40 (m, 1H), 5.42 (m, 1H), 5.69 (m, 1H), 6.99 (m, 1H), 7.23 (m, 6H), 7.53 (m, 1H), 8.20 (m, 1H); $^{31}$P NMR (CD$_3$OD) δ −2.92, −2.03; ESI-HRMS [M+Na]$^+$ C$_{39}$H$_{58}$$^{81}$BrN$_2$O$_{10}$PNa calcd for m/z 849.2889, found 849.2894.

(2S,3R,4E)-2-Amino-3-hydroxyoctadec-4-enyl-(4'-bromo-5'-hydroxy-2'-nitrophenyl)(phenyl)methyl Hydrogen Phosphate (2). A solution of 19 (25 mg, 0.030 mmol) in 3 M HCl/MeOH/CH$_2$Cl$_2$ (1:2:1, 4 mL) was stirred at gentle reflux (50-60° C.) for 2.5 h. The reaction mixture was diluted with CH$_2$Cl$_2$ (30 mL) and washed with brine (10 mL). The organic layer was dried (Na$_2$SO$_4$) and concentrated. Column chromatography (CHCl$_3$/MeOH 6:1, then 3:1), followed by removal of suspended silica gel by filtration of a solution of 2 in CHCl$_3$ through a 0.45-□m syringe filter, afforded 2 (12 mg, 60%) as a yellow solid: R$_f$ 0.35 (CHCl$_3$/MeOH 3:1); $^1$H NMR (CD$_3$OD) δ 0.89 (t, 3H, J=7.0 Hz), 1.28 (m, 22H), 2.03 (m, 2H), 2.95 (m, 1H), 3.59 (m, 1H), 3.75 (m, 1H), 4.07 (m, 1H), 5.28 (dd, 1H, J=6.5, 15.4 Hz), 5.70 (dt, 1H, J=6.7, 14.7 Hz), 7.02 (m, 1H), 7.25 (m, 5H), 7.44 (m, 1H), 8.25 (m, 1H); $^{13}$C DEPT-45 NMR (CD$_3$OD) 67 14.5, 23.7, 30.2, 30.4, 30.5, 30.6, 30.7, 30.8, 33.1, 33.3, 57.0, 63.3, 70.6, 76.4, 116.8, 127.8, 128.8, 129.0, 129.2, 129.3, 129.4, 131.8, 136.3, 136.8; $^{31}$P NMR (CD$_3$OD) 67 −1.41, −1.20; ESI-HRMS [M-H]$^-$ $^C{_{31}}$H$_{45}$BrN$_2$O$_8$P calcd for m/z 683.2096, found 683.2095; UV: λ$_{max}$ 406 nm (ϵ=12,000 M$^{-1}$cm$^{-1}$), 278 nm (ϵ=6,294 M$^{-1}$cm$^{-1}$) in 50% aq EtOH, 50% 10 mM Tris, pH 7.4.

Absorption Spectra of DECM-caged S1P and C1P Analogues. DECM-caged S1P 1 shows a λ$_{max}$ at 376 nm (ϵ=15,792 M$^{-1}$cm$^{-1}$) in EtOH. DECM-caged C1P 1a shows a λmax at 376 nm (ϵ=15,466 M$^{-1}$cm$^{-1}$) in CH$_2$Cl$_2$.

Qualitative Measurement of Uncaging Efficiency. A 100 μM solution of S1P 1 in 50% aqueous EtOH and 50% 10 mM Tris, pH 7.4, was placed in a quartz cuvette and placed at a distance of 1 cm from a conventional UV lamp (Entela UVGL-25 UV lamp). The compound was irradiated using long wavelength (365 nm) and, after a certain time, as indicated in the TLC, an aliquot was applied to a TLC plate, which was developed with CHCl$_3$/MeOH 3:1. Photodecomposition of 100% DECM-caged 1P 1 took place around 60 min.

Absorption Spectra of BHNB-caged SEP and C1P Analogues. BHNB-caged S1P 2 absorbs at 406 nm (ϵ=12,000 M$^{-1}$cm$^{-1}$) and 278 nm (ϵ=6,294 M$^{-1}$cm$^{-1}$) in 50% aqueous EtOH, 50% 10 mM Tris, pH 7.4. BHNB-caged C1P 2a absorbs at 397 nm (ϵ=1,747 M$^{-1}$cm$^{-1}$) and 320 nm (ϵ=4,111 M$^{-1}$cm$^{-1}$) in EtOH.

Stability of BHNPB-caged S1P (2) in Buffer in the Dark. The stability of BHNB-caged S1P (2) in 50% aqueous EtOH, 50% 10 mM Tris (170 μM), pH 7.4, was tested by withdrawing aliquots from the solution over a period of seven days. The analysis showed no change in the R$_f$ value (0.35, CHCl$_3$/MeOH 3:1) of the product, and no new spot was observed.

Qualitative Measurement of Uncaging Efficiency. A 100 μM solution of BHNB-caged S1P (2) in 50% aqueous EtOH and 50% 10 mM Tris, pH 7.4, was placed in a quartz cuvette and irradiated at 365 nm at a distance of 1 cm with a conventional UV lamp (Entela UVGL-25 UV lamp). Aliquots were withdrawn at various times and analyzed by TLC (developed using CHCl$_3$/MeOH 2:1). The mechanism of photolysis of 2-nitrobenzyl caged compounds has been thoroughly studied and is known to generate 2-nitrosobenzaldehyde as the photo by-product of the reaction.[S1] Similarly, our BHNB uncaging experiment is expected to generate a 2-nitrosobenzophenone derivative as the byproduct (Formula 20). After being photoirradiated for 65 min, the sample in the cuvette was concentrated and analysis by ESI-HRMS showed a strong peak at m/z 327.9596 (M+Na)⁺, which is the expected mass of the photo by-product. 100% photodecomposition of BIANB-S1P (2) took place after 65 min.

Formula 20. Uncaged photo-byproduct, 4-bromo-5-hydroxy-2-nitrosobenzophenone.

ESI-HRMS [M+Na]⁺ $C_{13}H_8{}^{79}BrNO_3Na$ calcd for m/z 327.9585, found 327.9596

Figure 1B:
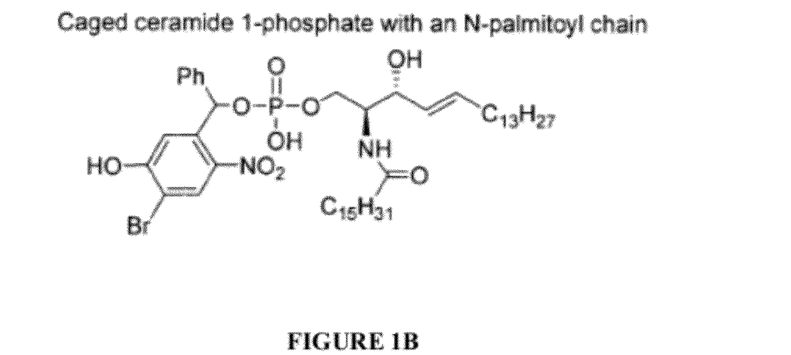
FIG. 1B shows the structure of caged ceramide l-phosphate with 4-bromo-5-hydroxy-2-nitrobenzhydryl (BHNB) group in a photolabile ester bond.

Cell Growth and Proliferation Assays. RAW 264.7 cells were obtained from the American Type Culture Collection (Rockville, Md.). BMDMs were isolated from femurs of 6- to 8-week old female CD-1 mice from Charles River Laboratory as described previously.[S2] The cells were cultured as described previously. Cell growth was estimated by measuring the rate of reduction of the tetrazolium dye MTS, (3-(4,5-dimethylthiazol-2-yl)-5-(3-carboxymethoxy-phenol)-2-(4-sulfophenyl)-2H-tetrazolium). Aqueous dispersions of commercial N-palmitoyl-C1P were prepared by sonication and added to the cultured macrophages as described previously.[S3,S4] FIG. 1 shows that the optimum concentration of exogenous N-palmitoyl-C1P for stimulation of RAW 264.7 macrophage cell growth was 30 µM; higher concentrations than 30 µM are growth inhibitory. Photolysis of 2.5 µM of compound 1a (delivered to RAW 264.7 cells in EtOH) was equipotent as exogenous 30 µM C1P.

Figure 4:
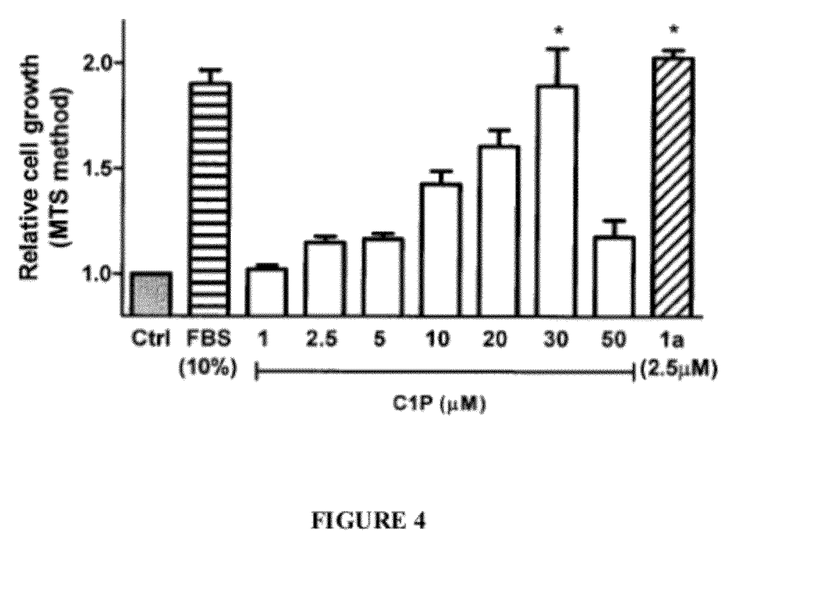
FIG. 4 shows the stimulation of growth of RAW 264.7 cells on addition of FBS, exogenous N-palmitoyl-C1P, and compound.

FIG. 4 shows the stimulation of growth of RAW 264.7 cells on addition of FBS, exogenous N-palmitoyl-CIP, and compound 1a. The cells were exposed to 400-500 nm light in a transilluminator equipped with a 9W lamp for 60 min at a distance of 1.5 cm at 37° C.

General Experimental Methods. The solvents were dried as follows. THF and Et₂O were heated at reflux over sodium benzophenone ketyl. Acetonitrile, diisopropylethylamine, and CH₂Cl₂ were distilled over calcium hydride, benzene was distilled over sodium metal, and methanol was heated at reflux over magnesium. Silica gel 60 F254 aluminum TLC plates of 0.2-mm thickness were used to monitor the reactions, with short wavelength ultraviolet light to visualize the spots and by charring the TLC plate after spraying with 15% sulfuric acid. Phosphorus-containing compounds were detected with a molybdic acid spray. Flash chromatography was carried out with silica gel 60 (230-400 ASTM mesh). ¹H NMR spectra were recorded at 400 and 500 MHz, and chemical shifts are given in parts per million. ¹³C NMR and ³¹P NMR spectra were recorded at 100 MHz and 162 MHz, respectively.

Syntheses (S)-tert-Butyl-4-formyl-2,2-dimethyloxazolidine-3-carboxylate (3). A solution of N-Boc-(S)-serine methyl ester (12.0 g, 46.3 mmol) in toluene (100 mL) was cooled to −78° C. under nitrogen. To the cooled solution was slowly added DIBAL-H (83 mL, a 1.5 M solution in toluene). The reaction mixture was stirred for 2 h at −78° C., and the reaction was quenched by slowly adding 100 mL of cold MeOH. The resulting white emulsion was slowly poured into 200 mL of ice-cold 1 M HCl with swirling over 20 min, and the aqueous mixture was extracted with EtOAc (3×120 mL). The combined organic layers were washed with brine (150 mL), dried (Na₂SO₄), and concentrated to give the crude product as a colorless oil, which was vacuum distilled to provide aldehyde 3 (7.5 g, 71%) as a colorless liquid, by 115-125 ° C. (9.0 mm Hg).

(S)-tert-Butyl-4-((R)-1-hydroxyallyl)-2,2-dimethyloxazolidine-3-carboxylate (4). To a −78° C. solution of (S)-Garner aldehyde (3, 7.0 g, 30.5 mmol) in dry THF (50 mL) under N₂ was slowly added vinylmagnesium bromide (92 mL, 92 mmol, a 1 M solution in THF) via cannula. After the cloudy yellow solution was stirred for 2 h at −78° C., it was warmed to 0° C., and the reaction was quenched with saturated aqueous NH₄Cl solution (60 mL). The product was extracted with Et₂O (2×60 mL). The combined organic layers were washed with brine (60 mL), dried (Na₂SO₄), and concentrated. The mixture of erythro and threo diastereomers was separated by column chromatography by gravity (hexane/EtOAc 5:1) to afford 4 (4.8 g, 62%) and its C3-epimer 4a (0.8 g, 10.2%). Compound 4: $[\alpha]^{25}_D$ −37.7° (c 1.8, CHCl₃); R_f 0.26 (EtOAc/hexane 1:3); ¹H NMR (CDCl₃) δ 1.48 (s, 3H), 1.50 (s, 9H), 1.58 (s, 3H), 3.91 (m, 2H), 3.98 (m, 1H), 4.25 (m, 1H), 4.39 (m, 1H), 5.24 (m, 1H), 5.38 (m, 1H), 5.85 (m, 1H); ¹³C NMR (CDCl₃) δ 24.2, 26.3, 28.3, 61.8, 64.4, 73.3, 81.4, 94.4, 116.1, 117.8, 137.6, 155.0; ESI-HRMS [M+Na]⁺ $C_{13}H_{23}NO_4Na$ calcd for m/z 280.1525, found 280.1519.

tert-Butyl-(2S,3R)-1-hydroxy-3-(methoxymethoxy)pent-4-en-2-yl-carbamate (6). To a solution of allylic alcohol 4 (900 mg, 3.5 mmol) in CH₂Cl₂ (25 mL) were added DIPEA (1.5 mL, 8.7 mmol) and MOMCl (0.56 mL, 7.0 mmol) at 0° C. After 10 min, the cooling bath was removed, and the reaction mixture was stirred overnight at rt. After TLC indicated the complete protection of the alcohol, the reaction mixture was diluted with saturated aqueous NH₄Cl solution (40 mL) and the product was extracted with CH₂Cl₂ (2×30 mL). The combined organic extracts were dried (Na₂SO₄) and concentrated to afford the MOM-protected alcohol 5 (960 mg, 91%). Without further purification, compound 5 (960 mg, 3.2 mmol) was dissolved in THF (25 mL), and 1 M HCl (5 mL) was added. The reaction mixture was stirred at rt until the starting material disappeared (overnight). The acid was neutralized by washing with saturated aqueous NaHCO₃ (30 mL) and the product was extracted with CH₂Cl₂ (2×25 mL). The organic layer was purified by chromatography (hexane/EtOAc 3:1) to afford alcohol 6 (705 mg, 85%): R_f 0.20 (EtOAc/hexane 1:3); ¹H NMR (CDCl₃) δ 1.44 (s, 9H), 3.21 (br s, 1H), 3.39 (s, 3H), 3.68 (m, 2H), 3.88 (dd, 1H, J=4.2, 11.6 Hz), 4.27 (t, 1H, J=5.0 Hz), 4.57 (d, 1H, J=6.6 Hz), 4.65 (d, 1H, J=6.6 Hz), 5.32 (m, 3H), 5.77 (m, 1H); ¹³C NMR (CDCl₃) δ 28.9, 54.6, 55.4, 62.0, 76.0, 78.3, 79.4, 94.0, 119.0, 134.7, 156.3; ESI-HRMS [M+Na]⁺ $C_{12}H_{23}NO_5Na$ calcd for m/z 284.1474, found 284.1468.

tert-Butyl-(2S,3R,4E)-1-hydroxy-3-(methoxymethoxy)octadec-4-en-2-yl-carbamate (7). To a solution of alcohol 6 (230 mg, 0.88 mmol) in CH₂Cl₂ (8 mL) was added 1-pentadecene (741 mg, 3.52 mmol). The solution was degassed twice using N₂ (2×10 min). To the reaction mixture was added benzylidene[1,3-bis(2,4,6-trimethyl-phenyl)-2-imidazolidinylidene]dichloro-(tricyclohexylphosphine)ruthenium catalyst (22.4 mg, 0.026 mmol) at rt under N₂. After the reaction mixture was stirred for 4 h under reflux, the solvent was removed and the product was purified by chromatography (hexane/EtOAc 4:1) to afford 7 (280 mg, 72%): R_f 0.45 (EtOAc/hexane 1:3); ¹H NMR (CDCl₃) δ 0.88 (t, 3H, J=7.0 Hz), 1.25 (m, 24H), 1.44 (m, 9H), 2.06 (q, 2H, J=7.7 Hz), 2.89

(d, 1H, J=5.2 Hz), 3.38 (s, 3H), 3.67 (m, 2H), 3.94 (dt, 1H, J=3.2, 11.1 Hz), 4.22 (dd, 1H, J=5.0, 7.6 Hz), 4.53 (d, 1H, J=6.6 Hz), 4.67 (d, 1H, J=6.6 Hz), 5.26 (d, 1H, J =7.6 Hz), 5.36 (dd, 1H, J=8.0, 15.4 Hz), 5.75 (dt, 1H, J=6.6, 14.6 Hz); $^{13}$C NMR (CDCl$_3$) δ 14.1, 22.7, 28.4, 29.0, 29.1, 29.3, 29.4, 29.6, 29.7, 31.9, 32.3, 54.9, 55.6, 62.3, 76.1, 78.3, 79.4, 93.8, 125.9, 136.9, 155.9; ESI-HRMS [M+Na]$^+$C$_{25}$H$_{49}$NO$_5$Na calcd for m/z 466.3508, found 466.3514.

tert-Butyl-(2S,3R,4E)-1-[7-diethylaminocoumarin-4-yl -methoxy(methoxy)phosphor-yloxy]-3-(methoxymethoxy) octadec-4-en-2-yl -carbamate (10). To a solution of compound 7 (55 mg, 0.124 mmol) in THF (8 mL) was added DIPEA (86.4 μL, 0.49 mmol). Methyl diisopropylphosphoramidochloridite (48 μL, 0.24 mmol) was added dropwise to the reaction mixture at 0° C. under N$_2$. After the reaction mixture was stirred at the same temperature for 30 min, H$_2$O (10 mL) was added, and the product was extracted with EtOAc (2×10 mL). The organic layer was dried (Na$_2$SO$_4$), concentrated, and the residue was purified by flash chromatography (hexane/EtOAc 3:1) to afford phosphoramidite 8: R$_f$0.68 (hexane/ EtOAc 3:1); $^{31}$P NMR (CDCl$_3$) δ 140.8. 7-(Diethylamino)- 4-hydroxymethylcoumarin (9) was prepared from 4-methyl- 7-(diethylamino)coumarin by a known procedure.[S5,S6] A mixture of coumarin 9 (71 mg, 0.28 mmol) and phosphoramidite 8 (58 mg, 0.096 mmol) was dried by lyophilization from benzene, and the residue was dissolved in CH$_3$CN (8 mL). The resulting solution was transferred by cannula to a solution of 1H-tetrazole (34 mg, 0.48 mmol) in CH$_3$CN (3 mL) at rt. After 3 h, the consumption of the phosphoramidite was complete as observed by TLC (hexane/EtOAc 3:1). To the intermediate phosphite, t-BuOOH (0.14 mL, a 1 M solution in toluene, 0.14 mmol) was added at 0° C., and the reaction mixture was warmed to rt. After 4 h, TLC indicated the complete conversion of the phosphite to the corresponding phosphate. The reaction mixture was diluted with CH$_2$Cl$_2$ (20 mL) and washed with saturated aqueous NaHCO$_3$ solution (15 mL). The organic layer was dried (Na$_2$SO$_4$), concentrated, and the residue was purified by chromatography (hexane/EtOAc 2:1) to afford phosphate 10 (52 mg, 55%): [α]$^{25}_D$ −26.5° (c 0.6, CHCl$_3$); R$_f$0.22 (EtOAc/hexane/Et$_3$N 48:50:2); $^1$H NMR (CDCl$_3$) δ 0.88 (t, 3H,J =6.6 Hz), 1.20 (t, 6H, J=7.1 Hz), 1.25 (m, 23H), 1.41 (s, 9H), 2.03 (q, 2H, J =6.5 Hz), 3.35 (s, 3H), 3.42 (q, 4H, J=7.1 Hz), 3.84 (d, 3H, J=10.5 Hz), 3.91 (br s, 1H), 4.09 (t, 1H, J=7.2 Hz), 4.25 (m, 1H), 4.31 (m, 1H), 4.50 (d, 1H, J=6.6 Hz), 4.69 (d, 1H, J=6.6 Hz), 4.95 (t, 1H, J=6.4 Hz), 5.20 (m, 2H), 5.29 (dd, 1H, J=8.4, 15.0 Hz), 5.75 (dt, 1H, J=5.9, 14.1 Hz), 6.21 (s, 1H), 6.50 (d, 1H, J=2.4 Hz), 6.58 (dd, IH, J=2.5, 9.0 Hz), 7.29 (d, 1H, J=9.0 Hz); $^{13}$C NMR (CDCl$_3$) δ 8 12.4, 14.1, 22.7, 28.3, 29.0, 29.2, 29.3, 29.4, 29.6, 29.7, 31.9, 32.3, 44.7, 54.7, 54.8, 55.7, 64.6, 67.0, 76.2, 79.6, 93.5, 97.8, 105.5, 106.3, 108.7, 124.3, 125.6, 138.1, 149.1, 150.7, 155.4, 156.2, 161.7; $^{31}$P NMR (CDCl$_3$) δ 0.43; ESI-HRMS [M+Na]$^+$C$_{40}$H$_{67}$N$_2$O$_{10}$PNa calcd for m/z 789.4431, found 789.4417.

(2S,3R,4E)-2-Amino-3-hydroxyoctadec-4-enyl (7-(Diethylamino)coumarin-4-yl) -methyl Phosphate (1). To a solution of phosphate 10 (25 mg, 0.032 mmol) in THF (1 mL) was added 6 M HCl (2 mL). The reaction mixture was stirred at 60° C. for 6 h. The reaction mixture was diluted with CH$_2$Cl$_2$ (10 mL) and brine (10 mL). The product was extracted with CH$_2$Cl$_2$ (3×15 mL), dried (K$_2$CO$_3$), and purified by chromatography (CHCl$_3$/MeOH 6:1). After removal of suspended silica gel by filtration of a solution of 1 in CHCl$_3$ through a 0.45-μm Cameo 30F syringe filter, compound 1 was obtained (15.5 mg, 78%): [α]$^{25}_D$ +2.22° (c 0.6, CHCl$_3$/MeOH 1:1); R$_f$ 0.70 (CHCl$_3$/MeOH/H$_2$O 65:35:8); $^1$H NMR (CDCl$_3$) δ 0.87 (t, 3H, J=5.5 Hz), 1.23 (m, 26H), 1.48 (m, 2H), 1.98 (q, 2H, J=5.9 Hz), 3.20-3.79 (m, 9H), 4.15 (m, 2H), 4.41 (m, 1H), 5.07 (m, 2H), 5.40 (dd, 1H, J=5.4, 15.2 Hz), 5.81 (dt, 1H, J=5.6, 13.4 Hz), 6.26 (s, 1H), 6.41 (s, 1H), 6.51 (d, 1H, J=8.0 Hz), 7.29 (d, 1H, J=8.0 Hz); $^{13}$C NMR (CDCl$_3$) δ 6 12.3, 14.0, 22.6, 28.2, 29.0, 29.3, 29.4, 29.6, 31.8, 32.3, 44.6, 55.8, 62.4, 63.1, 69.6, 97.3, 104.7, 108.8, 124.4, 126.2, 135.5, 150.6, 155.8, 163.0; $^{31}$P NMR (CDCl$_3$) δ −0.38; ESI-HRMS [M+H]$^+$ C$_{32}$H$_{54}$N$_2$O$_7$P calcd for m/z 609.3669, found 609.3670; UV: λ$_{max}$ 376 nm (ε=15792 M$^{-1}$cm$^{-1}$) in EtOH.

(2S,3R,4E)-2-Palmitamido-3-hydroxyoctadec-4-enyl (7-Diethylamino)coumarin-4-yl)methyl Phosphate (1a). A solution of compound 1 (7.0 mg, 0.010 mmol), p-nitrophenyl palmitate (9.4 mg, 0.023 mmol), and anhydrous potassium carbonate (3.6 mg, 0.024 mmol) was suspended in a solution of anhydrous DMF (2.5 mL) and CH$_2$Cl$_2$ (1 mL). After the reaction mixture had stirred for two days, the mixture was concentrated under high vacuum. The product was purified by chromatography (CHCl$_3$/MeOH 9:1), followed by removal of suspended silica gel by filtration of a solution of la in CHCl$_3$ through a 0.45-μm Cameo 30F syringe filter, affording DECM-caged ceramide 1-phosphate 1a (7.0 mg, 82%) as a yellow solid: R$_f$0.60 (CHCl$_3$/MeOH 2:1); [α]$^{25}_D$ +4.73° (c 0.27, CHCl$_3$:MeOH 1:1); R$_f$0.62 (CHCl$_3$/MeOH 2:1); $^1$H NMR (CDCl$_3$) δ 0.87 (t, 6H, J=6.5 Hz), 1.16-1.53 (m, 46H), 1.96 (q, 2H, J=6.9 Hz), 2.13 (t, 1H, J =7.3 Hz), 3.38 (m, 4H), 3.88 (m, 1H), 4.01 (m, 1H), 4.12 (t, 1H, J=7.2 Hz), 4.26 (m, 1H), 5.04 (m, 2H), 5.44 (dd, 1H, J=7.2, 14.8 Hz), 5.70 (dt, 1H, J=6.3, 14.1 Hz), 6.28 (s, 1H), 6.43 (s, 1H), 6.54 (d, 1H, J=8.0 Hz), 7.27 (d, 1H, J=8.3 Hz); $^{13}$C NMR (CDCl$_3$) δ 14.0, 22.6, 22.9, 23.6, 25.8, 28.8, 29.2, 29.3, 29.4, 29.5, 29.6, 29.7, 30.2, 31.9, 32.4, 36.4, 38.6, 44.6, 68.2, 97.4, 105.8, 108.8, 128.7, 130.9, 132.2, 134.7, 150.6, 155.8, 163.3, 167.9, 174.2; $^{31}$P NMR (CDCl$_3$) δ −0.83; ESI-HRMS (M+H)$^+$ C$_{48}$H$_{84}$N$_2$O$_8$P calcd for m/z 847.5965, found 847.5973; UV: λ$_{max}$ 376 nm (ε=15466 M$^{-1}$cm$^{-1}$) in EtOH.

1-Bromo-2-methoxy-4-methyl-5-nitrobenzene (12). To a solution of nitrobenzene 11 (2.2 g, 13.1 mmol) in CH$_3$CN (8 mL) in a pressure tube was added N-bromosuccinimide (8.2 g, 45.8 mmol). The tube was sealed and the contents were heated to 140° C. overnight on an oil bath. The reaction mixture turned brownish-red overnight. After the reaction was quenched with saturated aqueous Na$_2$S$_2$O$_3$ solution (150 mL), the product was extracted with Et$_2$O (2×150 mL), dried (Na$_2$SO$_4$), and purified by chromatography (hexane/EtOAc 3:1) to afford brominated product 12 along with other byproducts that were not separable by chromatography (hexane/ EtOAc 3:1). The product mixture (2.8 g, 87%) was used directly in the next step: R$_f$0.29 (hexane/EtOAc 3:1); $^1$H NMR (CDCl$_3$) δ 2.66 (s, 3H), 3.98 (s, 3H), 6.76 (s, 1H), 8.31 (s, 1H); $^{13}$C NMR (CDCl$_3$) δ 21.7, 56.8, 108.9, 114.3, 125.2, 130.4, 136.3, 141.9, 159.3; ESI-HRMS [M-Br—CH$_3$—H]$^-$ C$_7$H$_6$NO$_3$ calcd for m/z 152.0348, found 152.0349.

4-Bromo-5-methoxy-2-nitrobenzaldehyde (13). To a stirred solution of compound 12 (2.3 g, 9.4 mmol) in dry DMF (15 mL) was added N,N-dimethylformamide dimethyl acetal (DMF·DMA) (6.0 g, 24.5 mmol). After the reaction mixture was heated at 140° C. for 16 h, the dark red solution was cooled to 0° C. and added rapidly to a stirred solution of NaIO$_4$ (10.5 g, 49 mmol) in H$_2$O/DMF (4:1, 25 mL) at 0° C. After 8 h of stirring, the brown solution was filtered, and the reaction flask was rinsed with toluene/EtOAc (1:1, 30 mL) and again filtered. The filtrate was washed with saturated aqueous NaCl solution (45 mL) and extracted with EtOAc (2×45 mL). The organic phase was dried (Na$_2$SO$_4$) and concentrated, and the residue was purified by flash chromatography (hexane/EtOAc 3:1) to afford aldehyde 13 (1.3 g, 54%): R$_f$0.22 (hexane/EtOAc 3:1); $^1$H NMR (CDCl$_3$) δ 4.09 (s, 3H), 7.38 (s, 1H), 8.43 (s, 1H), 10.50 (s, 1H); $^{13}$C NMR (CDCl$_3$) δ 57.4, 110.5, 116.8, 130.3, 132.6, 142.3, 160.5, 187.7; ESI-HRMS [M-H]$^-$C$_8$H$_5$$^{79}$BrNO$_4$ calcd for m/z 257.9402, found 257.9407.

(4-Bromo-5-methoxy-2-nitrophenyl)(phenyl)methanol (14). To a solution of aldehyde 13 (200 mg, 0.77 mmol) in THF (10 mL) at −78° C. was added slowly a solution of PhMgBr (2.7 mL, a 1.0 M solution in THF, 2.7 mmol). After the reaction mixture was stirred at this temperature for 30 min, the reaction was quenched with 1 M HCl (15 mL). The product was extracted with Et$_2$O (2×20 mL). The organic layer was dried (Na$_2$SO$_4$), and concentrated, and the residue was purified by flash chromatography (hexane/EtOAc 3:1) to afford 14 (240 mg, 92%): R$_f$ 0.32 (hexane/EtOAc 3:1); $^1$H NMR (CDCl$_3$) δ 2.96 (br s, 1H), 3.96 (s, 3H), 6.52 (s, 1H), 7.27 (m, 5H), 7.37 (s, 1H), 8.28 (s, 1H); $^{13}$C NMR (CDCl$_3$) δ 57.0, 71.7, 110.5, 110.9, 127.1, 128.3, 128.7, 130.6, 140.6, 141.2, 160.0: ESI -HRMS [M+HCO$_2$]$^-$ C$_{15}$H$_{13}$$^{79}$BrNO$_6$ calcd for m/z 381.9926, found 381.9931.

(4S,5R,1'E)-tert-Butyl-4-(hydroxymethyl)-2,2-dimethyl-5-(pentadec-1'-enyl)-oxazolidine-3-carboxylate (16).$^{S7}$ To a solution of D-erythro-sphingosine (400 mg, 1.3 mmol) in EtOH/H$_2$O (2:1, 9 mL) was added aqueous 1 N NaOH (3.9 mL, 3.9 mmol) and (Boc)$_2$O (851 mg, 3.9 mmol). The reaction mixture was stirred at rt until the consumption of the starting material was observed by TLC (hexane/EtOAc 3:1): R$_f$ 0.12. The reaction was quenched with saturated aqueous NH$_4$Cl solution (30 mL), and the product was extracted with EtOAc (2×25 mL), dried (Na$_2$SO$_4$), and concentrated. The resulting residue was purified by flash chromatography (hexane/EtOAc 3:1) to afford the N-Boc-sphingosine derivative (495 mg, 95%): R$_f$ 0.22. The Boc derivative (180 mg, 0.45 mmol) was thoroughly dried in vacuum and then was dissolved in CH$_2$Cl$_2$ (10 mL). After imidazole (122 mg, 1.8 mmol) and TBDPSCl (236 μL, 0.90 mmol) were added, the reaction mixture was stirred for 3 h at rt, and then was concentrated. The residue was purified by flash chromatography (hexane/EtOAc 3:1): R$_f$ 0.65. To a solution of the silylated primary alcohol in benzene (30 mL) were added 2,2-dimethoxypropane (220 μL, 1.8 mmol) and catalytic p-TsOH.H$_2$O (1 mg, 0.010 mmol). The reaction mixture was heated at reflux in a Dean-Stark trap for 30 min. The reaction was quenched with saturated aqueous NaHCO$_3$ solution (15 mL), and the product was extracted with EtOAc (2×15 mL), dried (Na$_2$SO$_4$), concentrated, and purified by flash chromatography (hexane/EtOAc 3:1) to afford the isopropylidene derivative: R$_f$ 0.75. The isopropylidene intermediate was treated with TBAF (11.25 mL, 1 M solution in THF, 11.25 mmol) for 6 h at rt. The reaction mixture was diluted with H$_2$O (10 mL), and the product was extracted with EtOAc (2×15 mL), dried (Na$_2$SO$_4$), concentrated, and purified by flash chromatography (hexane/EtOAc 3:1) to afford protected sphingosine derivative 16 (92 mg, 47%): R$_f$ 0.51 (hexane/EtOAc 3:1); $^1$H NMR (CDCl$_3$) δ 0.88 (t, 3H, J=6.8 Hz), 1.26 (m, 22H), 1.49 (s, 9H), 1.54 (s, 3H), 1.60 (s, 3H), 2.07 (q, 2H, J=5.6 Hz), 3.50 (br s, 1H), 3.65 (m, 1H), 3.80 (m, 1H), 4.09 (m, 1H), 4.57 (m, 1H), 5.46 (dd, 1H, J=7.5, 15.2 Hz), 5.88 (dt, 1H, J=6.5, 13.8 Hz); $^{13}$C NMR (CDCl$_3$) δ 14.1, 22.7, 24.7, 27.8, 28.4, 28.8, 29.2, 29.3, 29.4, 29.5, 29.7, 31.9, 62.0, 63.8, 81.2, 92.9, 123.2, 137.5, 154.4; ESI -HRMS [M+Na]$^+$ C$_{26}$H$_{49}$NNaO$_4$ calcd for m/z 462.3559, found 462.3554.

(4S,5R,1''E)-tert-Butyl-4-((((4'-bromo-5'-methoxy-2'-nitrophenyl)(phenyl)methoxy)(methoxy)phosphoryloxy)methyl)-2,2-dimethyl-5-(pentadec-1''-enyl)oxazolidine-3-carboxylate (18). To a solution of compound 14 (44 mg, 0.13 mmol) in THF (8 mL) was added DIPEA (54 μL, 0.31 mmol). Methyl diisopropyl phosphoramidochloridite (51 μL, 0.26 mmol) was then added slowly to the reaction mixture at rt under N$_2$. After the reaction mixture was stirred at the same temperature for 3 h, H$_2$O (8 mL) was added and the product was extracted with EtOAc (2×8 mL). The organic layer was dried (Na$_2$SO$_4$), concentrated, and the product was purified by flash chromatography (hexane/EtOAc 3:1) to afford phosphoramidite 15: R$_f$ 0.65 (hexane/EtOAc 3:1). A mixture of phosphoramidite 15 (52 mg, 0.10 mmol) and protected sphingosine 16 (88 mg, 0.20 mmol) was dried by lyophilization from benzene, and the residue was dissolved in CH$_3$CN (5 mL). The resulting solution was transferred by cannula to a solution of 1H-tetrazole (21 mg, 0.30 mmol) in CH$_3$CN (3 mL) at rt. After 3 h, complete consumption of the phosphoramidite took place as observed by TLC (hexane/EtOAc 3:1). The reaction was quenched with saturated aqueous NaHCO$_3$ solution (10 mL), and the product was extracted with EtOAc (2×15 mL), dried (Na$_2$SO$_4$), concentrated, and purified by flash chromatography (hexane/EtOAc 3:1) to afford phosphite 17: R$_f$ 0.55. To the intermediate phosphite 17 was added t-BuOOH (0.3 mL, a 1 M solution in toluene) at rt. After 1 h, TLC indicated the complete conversion of the phosphite to the corresponding phosphate. The reaction mixture was concentrated and purified by chromatography (hexane/EtOAc 3:1) to afford phosphate 18 (60 mg, 70%): R$_f$ 0.15 (EtOAc/hexane 1:3); $^1$H NMR (CDCl$_3$) δ 0.88 (t, 3H, J=6.7 Hz), 1.26 (m, 22H), 1.46 (s, 9H), 1.53 (s, 3H), 1.64 (s, 3H), 2.07 (m, 2H), 3.64 (m, 3H), 3.86 (m, 1H), 3.99 (m, 1H), 4.06 (m, 4H), 4.50 (m, 1H), 5.48 (m, 1H), 5.88 (m, 1H), 7.25 (m, 1H), 7.32 (m, 6H), 7.51 (m, 1H), 8.37 (s, 11-1); $^{13}$C NMR (CDCl$_3$) δ 14.1, 22.7, 28.3, 29.0, 29.4, 29.5, 29.6, 29.7, 31.9, 32.5, 54.4, 57.1, 59.2, 80.3, 93.1, 110.0, 111.3, 122.8, 127.9, 128.0, 128.6, 129.0, 130.8, 137.9, 139.8, 160.1; $^{31}$P NMR (CDCl$_3$) δ −1.60, −1.46, −1.31, −1.13; ESI-HRMS [M+Na]$^+$ c$_{41}$H$_{62}$BrN$_2$O$_{10}$PNa calcd for m/z, 875.3223 found 875.3218.

(4'-Bromo-5'-hydroxy-2'-nitrophenyl)(phenyl)methyl-(2S,3R,4E)-3-hydroxy-2-palmitamidooctadee-4-enyl Hydrogen Phosphate (2a). A solution of compound 2 (1.0 mg, 1.5 μmol), p-nitrophenyl palmitate (1.7 mg, 4.5 μmol), and anhydrous potassium carbonate (1 mg, 4.5 μmol) was suspended in a solution of anhydrous DMF (1.25 mL) and CH$_2$Cl$_2$ (0.5 mL). After the reaction mixture had stirred for 2 days, the mixture was concentrated under high vacuum. The compound was purified by chromatography (CHCl$_3$/MeOH 6:1), followed by removal of suspended silica gel by filtration of a solution of compound 2a in CHCl$_3$ through a 0.45-μm 30F syringe filter, affording BHNB caged C1P 2a (1 mg, 77%): R$_f$ 0.33 (CHCl$_3$/MeOH 6:1); $^1$H NMR (CDCl$_3$/CD$_3$OD 30:1) δ 0.83 (t, 6H, J=6.8 Hz), 1.25 (m, 46H), 1.92 (m, 2H), 2.10 (m, 2H), 3.58 (m, 1H), 3.83 (m, 1H), 3.92 (m, 2H), 4.0 (m, 1H), 5.34 (m, 1H), 5.62 (m, 1H), 7.02 (m, 1H), 7.23 (m, 5H), 7.50 (m, 1H), 8.29 (m, 1H); $^{13}$C DEPT-45 NMR (CDCl$_3$/CD$_3$OD 30:1) δ 14.1, 19.8, 22.7, 29.3, 29.4, 29.5, 29.6, 29.7, 29.8, 30.2, 31.9, 32.4, 36.5, 53.5, 57.0, 71.4, 74.4, 77.4, 110.8, 127.5, 127.7, 128.2, 128.4, 130.3, 135.0; $^{31}$P NMR (CDCl$_3$/CD$_3$OD 30:1) δ −1.23, −1.11; ESI-HRMS [M+Na]$^+$ C$_{47}$H$_{76}$BrN$_2$O$_9$PNa calcd for m/z 945.4369, found 945.4363; UV: λ$_{max}$ 397 nm (ε=1,747 M$^{-1}$cm$^{-1}$), 320 nm (ε=4,111 M$^{-1}$cm$^{-1}$) in EtOH.

REFERENCES

S1. Zhao, Y.; Zheng, Q.; Dakin, K.; Xu, K.; Martinez, M. L.; Li, W. H. *J. Am. Chem. Soc.* 2004, 126, 4653.

S2. Gangoiti, P.; Granado, M. H.; Wang, S. W.; Kong, J. K.; Steinbrecher, U. P.; Gómez-Muñoz, A. *Cell. Signalling* 2008, 20, 726.

S3. Gómez-Muñoz, A.; Kong, J. Y.; Salh, B.; Steinbrecher, U. P. *J. Lipid Res.* 2004, 45, 99.

S4. Gómez-Muñoz, A.; Kong, J. Y.; Parhar, K.; Wang, S. W.; Gangoiti, P.; González, M.; Eivemark, S.; Salh, B.; Duronio, V.; Steinbrecher, U. P. *FEBS Lett.* 2005, 579, 3744.

S5. Schönleber, R. O.; Bendig, J.; Hagen, V.; Giese, B. *Bioorg. Med. Chem.* 2002, 10, 97.

S6. Ito, K.; Nakajima, K. *J. Heterocycl. Chem.* 1988, 25, 511.

S7. Qiao, L.; Kozikowski, A. P.; Olivera, A.; Spiegel, S. *Bioorg. Med. Chem. Lett.* 1998, 8, 711.

The invention claimed is:

1. A D-erythro ceramide-1-phosphate derivative represented by formula 1, (1)

$R_1$ represents the benzhydryl derivative of formula 2;
$R_3$ represents H or the benzhydryl derivative of formula 2;

(2)

n is 12 or 14
$R_2$ represents the fatty acyl group of formula 4

(4)

$R^4$ represents H or OH;
$R^5$ represents a saturated or unsaturated aliphatic group of 12-22 carbon atoms;
Y and Z independently represent H, Cl, Br, OH, OCH$_3$, or triazolyl, in which case at least one of Y or Z represents OH; or Y and Z on together to form a 5 or 6 member carbocyclic or heterocyclic ring that is optionally fused to a second 5 or 6 member carbocyclic or heterocyclic ring, wherein the second 5 or 6 member carbocyclic or heterocyclic ring is optionally fused to a third 5 or 6 member carbocyclic or heterocyclic ring, and wherein any of the carbocyclic or heterocyclic rings are optionally substituted with one or more functional groups selected from the group consisting of methyl, OH, OCH$_3$, Cl, Br, NO2, NMe$_2$, and NEt$_2$;
Ar$^1$ represents phenyl, or phenyl substituted with one or more functional groups selected from the group consisting of NMe$_2$, NEt$_2$, OH, and OCH$_3$.

2. The derivative according to claim 1, wherein $R^3$ and $R^4$ represent H.

3. The derivative according to claim 1, wherein Y and Z independently represent H, Cl, Br, OH, OCH$_3$, or triazolyl.

4. The derivative according to claim 3, wherein Y and Z independently represent Cl, Br, OH, or OCH$_3$.

5. The derivative according to claim 3, wherein Y and Z independently represent Br or OH.

6. The derivative according to claim 2, wherein Y represents OH and Z represents Br.

7. The derivative according to claim 6, wherein Ar$^1$ represents phenyl.

8. The derivative according to claim 7, wherein $R^5$ represents —(CH$_2$)$_{13}$—CH$_3$.

9. A method for introducing a ceramide-1-phosphate into a biological cell, the method comprising exposing the cell to a D-erythro ceramide-1-phosphate represented by formula 1, (1)

wherein:
$R_1$ represents the benzhydryl derivative of formula 2;
$R_3$ represents H or the benzhydryl derivative of formula 2;

(2)

n is 12 or 14
$R_2$ represents the fatty acyl group of formula 4:

(4)

$R^4$ represents H or OH;
$R^5$ represents a saturated or unsaturated aliphatic group of 12-22 carbon atoms;
Y and Z independently represent H, Cl, Br, OH, OCH$_3$, or triazolyl, in which case at least one of Y or Z represents OH; or Y and Z join together to form a 5 or 6 member carbocyclic or heterocyclic ring that is optionally fused to a second 5 or 6 member carbocyclic or heterocyclic ring, wherein the second 5 or 6 member carbocyclic or heterocyclic ring is optionally fused to a third 5 or 6 member carbocyclic or heterocyclic ring, and wherein any of the carbocyclic or heterocyclic rings are optionally substituted with one or more functional groups selected from the group consisting of methyl, OH, OCH$_3$, Cl, Br, NO2, NMe$_2$, and NEt$_2$;

Ar$^1$ represents phenyl, or phenyl substituted with one or more functional groups selected from the group consisting of NMe$_2$, NEt$_2$, OH, and OCH$_3$.

10. A method according to claim 9, wherein R$^3$ and R$^4$ represent H.

11. The method according to claim 9, wherein Y and Z independently represent H, Cl, Br, OH, OCH$_3$, or triazolyl.

12. The method according to claim 11, wherein Y and Z independently represent Cl, Br, OH, or OCH$_3$.

13. The method according to claim 11, wherein Y and Z independently represent Br or OH.

14. The method according to claim 10, wherein Y represents OH and Z represents Br.

15. A method according to claim 14, wherein Ar$^1$ represents phenyl.

16. A method according to claim 15, wherein R$^5$ represents —(CH$_2$)$_{13}$—CH$_3$.

\* \* \* \* \*